United States Patent [19]

Shima et al.

[11] Patent Number: 5,075,493

[45] Date of Patent: Dec. 24, 1991

[54] PROCESS FOR PREPARING α, β-UNSATURATED CARBOXYLIC ACID ESTER

[75] Inventors: Yoshikazu Shima; Takafumi Abe; Hirofumi Higuchi, all of Niigata; Koichi Kida, Tsukuba, all of Japan

[73] Assignee: Mitsubishi Gas Chemical Company, Inc., Tokyo, Japan

[21] Appl. No.: 618,040

[22] Filed: Nov. 23, 1990

[30] Foreign Application Priority Data

Mar. 15, 1990 [JP] Japan ................................. 2-62751

[51] Int. Cl.$^5$ .............................................. C07C 67/30
[52] U.S. Cl. .................................... 560/212; 562/599
[58] Field of Search ......................... 560/212; 562/599

[56]  References Cited

U.S. PATENT DOCUMENTS 2,376,704  5/1945  Kung ................................... 560/212
2,485,510  10/1949  Redmon .............................. 560/212
3,022,337  2/1962  Enk et al. ............................ 560/212
4,464,539  8/1984  Hashimoto .......................... 560/212

FOREIGN PATENT DOCUMENTS 196753  8/1990  Japan .

Primary Examiner—Paul J. Killos
Attorney, Agent, or Firm—Frishauf, Holtz, Goodman & Woodward

[57] ABSTRACT

A process for producing α, β-unsaturated carboxylic acid ester which comprises catalytically reacting α-hydroxycarboxylic acid ester with crystalline aluminosilicate catalyst, and then catalytic reacting the resulting reaction product with solid acid catalyst.

According to the process, α, β-unsaturated carboxylic acid ester of a high purity, and a high quality, without by-product, can be produced efficiently.

7 Claims, No Drawings

PROCESS FOR PREPARING α, β-UNSATURATED CARBOXYLIC ACID ESTER

BACKGROUND OF THE INVENTION

1. Field of the Invention

This invention relates to a process for preparing an α, β-unsaturated carboxylic acid ester, more particularly to a process for an efficient production in an industrial scale of an α,β-unsaturated carboxylic acid ester by using an α-hydroxycarboxylic acid ester as the starting material.

The α,β-unsaturated carboxylic acid ester is very useful in industry as a starting material for synthetic resins. In particular, methyl methacrylate obtained from methyl α-hydroxyisobutyrate has been used for an important industrial purpose, as a starting material for polymethyl methacrylate which has excellent weather resistance and transparency.

2. Description of the Related Arts

The present inventors' group previously disclosed a process for preparing an α,β-unsaturated carboxylic acid and/or an ester thereof by using at least one ester selected from the group consisting of α-hydroxycarboxylic acid ester, α-alkoxycarboxylic acid ester and β-alkoxycarboxylic acid ester as a starting material, and by catalytically reacting it with crystalline aluminosilicate catalyst (Japanese Patent Application Laid-Open No. 196753/1990).

Although the above process is remarkably efficient, α, β-unsaturated carboxylic acid and an ester thereof are produced simultaneously. Accordingly, operations for separating and recovering these products, such as distillation and extraction, are inevitable in the process. Since these operations cause an increase in production cost, more simple and economical process is desired to be developed.

SUMMARY OF THE INVENTION

The present inventors have intensively studied a process for a selective preparation of an α, β-unsaturated carboxylic acid ester, without forming α, β-unsaturated carboxylic acid in production of α, β-unsaturated carboxylic acid ester from α-hydroxycarboxylic acid ester. As the result, it was found that α, β-unsaturated carboxylic acid ester can be selectively obtained in a high yield, first by catalytically reacting α-hydroxycarboxylic acid ester with crystalline aluminosilicate catalyst, and subsequently by catalytically reacting the resultant product with a solid acid catalyst. The present invention has been accomplished based on such findings.

The present invention provides a process for producing an α, β-unsaturated carboxylic acid ester, which comprises catalytically reacting α-hydroxycarboxylic acid ester with crystalline aluminosilicate catalyst, and then catalytically reacting the resultant product with a solid acid catalyst.

As described above, the process of the present invention is a process in which α-hydroxycarboxy acid ester is catalytically reacted successively in the presence of crystalline aluminosilicate as the first catalyst and a solid acid catalyst as the second catalyst. In this manner, the production of α, β-unsaturated carboxylic acid and other by-products are inhibited, and an α, β-unsaturated carboxylic acid ester of high quality, having a low degree of coloration, can be produced selectively and in a high yield.

DESCRIPTION OF PREFERRED EMBODIMENTS

The process of the present invention is described in more detail as follows.

As the catalytic reaction of α-hydroxycarboxylic acid ester in the process of the present invention, all processes in which the starting material and the catalyst can be contacted can be employed, but preferred are processes with vapor phase reactions or vapor/liquid mixed phase reactions. Various reaction methods such as fixed-bed method or fluid-bed method, and batch system or continuous system can be employed.

The process of the present invention is particularly preferred to be carried out as follows. Into an α-hydroxycarboxylic acid ester as the starting material, an alcohol corresponding to the alkoxy portion of said ester is added as solvent to prepare the starting solution, and then the solution is contacted with the crystalline aluminosilicate catalyst in the first stage and then the resultant reaction mixture is catalytically reacted directly with the solid acid catalyst in the second stage. In this way, a high-quality α, β-unsaturated carboxylic acid ester can be obtained selectively and in a high yield. Examples of α-hydroxycarboxylic acid ester to be used there are methyl α-hydroxyisobutyrate and methyl lactate.

In the process of the present invention, when the object is merely to inhibit the production of α, β-unsaturated carboxylic acid, a starting solution containing a very excessive amount of alcohol as solvent can be used, but as the proportion of alcohol increases, the energy cost required to separate α, β-unsaturated carboxylic acid ester increases undesirably.

The proportion of alcohol as the solvent in the process of the present invention is not critical, and can be selected depending on circumstances, but usually it is 0 to 20 moles, preferably 1 to 10 moles to 1 mole of α-hydroxycarboxylic acid ester. In the process of the present invention, the reaction can proceed without any addition of solvent (that is, the proportion of alcohol is 0 mole).

The crystalline aluminosilicate as the first catalyst in the process of the present invention includes X-type zeolite and Y-type zeolite, and the typical zeolite is commercially available Molecular Sieve 13X (trade mark). The solid acid catalyst as the second catalyst includes a phosphate-containing catalyst, solid phosphoric acid catalyst, a sulfate-containing catalyst, and oxide catalysts such as silica-alumina, silica-titania, silica-zirconia, and zeolite.

As a preferred embodiment of the process of the present invention, the first stage of the tubular reactor is packed with crystalline aluminosilicate catalyst, and the second stage is packed with solid acid catalyst, each in a predetermined amount, and if necessary, a small amount of nitrogen is passed through as a carrier gas. The reaction temperature of the first stage is selected to be in the range of 150° to 450° C., preferably 200° to 350° C., and the reaction temperature of the second stage is selected in the range of 50° to 450° C., preferably 100° to 350° C. Furthermore, α-hydroxycarboxylic acid ester alone, or an alcohol solution of α-hydroxycarboxylic acid ester with a concentration of 10 or more % by weight, preferably 30 to 85% by weight, is supplied continuously to the reaction system as the starting material, to be catalytically reacted in each of the stages.

The α-hydroxycarboxylic acid ester as the starting material can be used singly, or as the mixture with α-alkoxycarboxylic acid ester or β-alkoxycarobxylic acid ester.

When the reaction product solution thus obtained is extracted or distilled, an α, β-unsaturated carboxylic acid ester of high quality can be easily separated and recovered. The unreacted starting material separated and recovered by these operations can be utilized again.

According to the process of the present invention, a catalytic reaction under mild conditions can be carried out using α-hydroxycarobxylic acid ester as the starting material, crystalline aluminosilicate as the catalyst in the first stage, solid acid catalyst in the second stage, to obtain a high quality α, β-unsaturated carboxylic acid ester selectively in a high yield. Therefore, the process of the present invention has great industrial significance.

The process of the present invention is described in greater detail with reference to the following examples and comparative examples, although it is not intended to be limited thereto.

EXAMPLE 1

In a quartz tubular reactor having an inner diameter of 15 mm and a length of 450 mm, the first stage and the second stage were packed with each 5 g of Molecular Sieve 13X and silica-titania (Si/Ti=85/15), respectively, and the temperature of the catalytic layer was kept at 240° C. in the first stage, and at 150° C. in the second stage. Methyl α-hydroxyisobutyrate solution in a concentration of 50% by weight dissolved in methanol as a solvent was vaporized through preheating layer at 5 g/hour, to be supplied into the catalyst layer.

As the result of analyzing the solution produced in 4 hours after the reaction started, the conversion of methyl α-hydroxyisobutyrate was 99.8%, and the selectivity to methyl methacrylate was 95.7%, and the selectivities to methacrylic acid, acetone and methyl α-methyloxyisobutyrate were each less than 1%.

Even though 24 hours elapsed after the reaction started, the conversion of methyl o-hydroxyisobutyrate was 99.2%, and the selectivity to methyl methacrylate was 96%. The coloration of the reaction product solution was 10 in APHA value.

EXAMPLES 2 TO 6

The procedure of Example 1 was repeated except that the catalyst shown in Table 1 was used in the second stage, and that the reaction temperature was set as shown in Table 1.

The selectivity to methyl methacrylate in each Example is as shown in Table 1, but the conversion of methyl α, β-hydroxyisobutyrate was 99.6% or more, and the coloration of the reaction product solution was less than 10 in APHA value.

TABLE 1

| Example | Kind of Catalyst | Reaction Temp. (°C.) | MMA* Selectivity (%) |
|---|---|---|---|
| 2 | 15% solid phosphoric acid/SiO$_2$.Al$_2$O$_3$ | 180 | 95.3 |
| 3 | MgSO$_4$ | 200 | 94.7 |
| 4 | SiO$_2$.Al$_2$O$_3$ | 180 | 94.9 |
| 5 | SiO$_2$.ZrO$_2$ | 150 | 95.5 |
| 6 | MS-13X** | 150 | 94.1 |

*MMA: methyl methacrylate
**MS-13X: Molecular Sieve 13X

COMPARATIVE EXAMPLE 1

The procedure of Example 1 was repeated except that no catalyst was packed in the second stage.

As the result, the conversion of methyl α-hydroxyisobutyrate was 99.6%, the selectivity to methyl methacrylate was 90.4%, the selectivity to methacrylic acid was 3.2%, and the selectivities of acetone and methyl α-methoxyisobutyrate were each about 1%, and the coloration of the reaction product solution was 50 in APHA value.

What is claimed is:

1. A process for producing α, β-unsaturated carboxylic acid ester which comprises catalytically reacting α-hydroxycarboxylic acid ester with crystalline aluminosilicate catalyst, and then catalytically reacting the resultant product with solid acid catalyst.

2. The process according to claim 1, wherein the crystalline aluminosilicate is X-type zeolite or Y-type zeolite.

3. The process according to claim 1, wherein the solid acid catalyst is a phosphate-containing catalyst, solid phosphoric acid catalyst, a sulfate-containing catalyst, silica-alumina, silica-titania, silica-zirconia or zeolite.

4. The process according to claim ,1, wherein α-hydroxycarboxylic acid ester is methyl α-hydroxyisobutyrate or methyl lactate.

5. The process according to claim 1, wherein alcohol corresponding to the alkoxy portion of α-hydroxycarboxylic acid ester as the starting material is used as the reaction solvent.

6. The process according to claim 1, wherein alcohol as the reaction solvent is used in the range of 1 to 10 moles to 1 moles of α-hydroxycarboxylic acid ester.

7. The process according to claim 1, wherein the temperature in the catalytic reaction with crystalline aluminosilicate catalyst is 150° to 450° C., and the temperature in the catalytic reaction with solid acid catalyst is 50° to 450° C.

* * * * *